United States Patent
Kitano

[11] Patent Number: 5,353,324
[45] Date of Patent: Oct. 4, 1994

[54] TOTAL REFLECTION X-RAY DIFFRACTION MICROGRAPHIC METHOD AND APPARATUS

[75] Inventor: Tomohisa Kitano, Tokyo, Japan

[73] Assignee: NEC Corporation, Tokyo, Japan

[21] Appl. No.: 865,269

[22] Filed: Apr. 8, 1992

[30] Foreign Application Priority Data

Apr. 22, 1991 [JP] Japan .................................. 3-118111

[51] Int. Cl.[5] ...................................... G01N 23/207
[52] U.S. Cl. ....................................... 378/73; 378/83; 378/84
[58] Field of Search ...................... 378/73, 74, 78-81, 378/71, 83

[56] References Cited

U.S. PATENT DOCUMENTS

3,051,834  8/1962  Shimula et al. .................. 378/80
4,928,294  5/1990  Beard, Jr. et al. ................ 378/74

OTHER PUBLICATIONS

"Theoretical Considerations on Bragg-Case Diffraction of X-rays at a Small Glancing Angle" (Seigo Kishino and Kazutake Kohra, Japanese Journal of Applied Physics, vol. 10, No. 5, pp. 551–557 (1971).

"On X-Ray Diffraction in an Extremely Asymmetric Case" (T. Bedynska, Phys. stat. sol. (a), 19, pp. 365–372 (1973)).

"On the Deviation from the Bragg Law and the Widths of Diffraction Patterns in Perfect Crystals" (F. Rustichelli, Philosophical Magazine, vol. 31, pp. 1–12 (1974 and 1975)).

"A Modified Dynamical Theory (MDT) of X-Ray Diffraction in Extremely Asymmetric Schemes" (A. M. Afansev and O. G. Melikyan, PHys. stat. sol. (a), 122, (1990)) pp. 459–468.

Primary Examiner—Craig E. Church
Attorney, Agent, or Firm—Burns, Doane, Swecker & Mathis

[57] ABSTRACT

A method for detecting and evaluating crystal defects existing in the extreme neighborhood of the surface of a crystal specimen through the use of X-ray analyzing micrography. Synchrotron radiation is used as the X-ray source. A monochromatic X-ray beam generated from the synchrotron radiation is directed into the crystal specimen at a glancing angle smaller than the critical angle of said crystal specimen relative to said monochromatic X-ray beam. The diffracted X-rays from the crystal specimen due to asymmetrical reflection are detected in order to observe the resulting diffracted image.

7 Claims, 4 Drawing Sheets

1

TOTAL REFLECTION X-RAY DIFFRACTION MICROGRAPHIC METHOD AND APPARATUS

BACKGROUND OF THE INVENTION

1. Field of the Invention

The present invention relates to a total reflection type X-ray diffraction micrographic method and an apparatus for implementing the same method, and in particular, to a total reflection type X-ray diffraction micrographic method and apparatus suitable for detecting crystal defects present on and within the surface of a semiconductor wafer.

2. Description of the Related Art

In a semiconductor wafer such as a single crystalline silicon wafer, crystal defects present therein or thereon (for example, voids, interstitial atoms, dislocations, random stacking, depositions, segregations or the like) can exert adverse effects on the characteristics of a semiconductor device produced from this semiconductor wafer. In view of this problem, numerous methods have been developed to detect and evaluate the crystal defects present in the interior or on the surface of semiconductor wafers.

As one of such methods, there has been available a method called X-ray diffraction microscopy or X-ray topography which utilizes a diffraction phenomenon of X-rays. FIG. 1 is a layout plan view illustrating an arrangement implemented when a silicon (100) wafer is measured in accordance with this method. Incident X-ray beam 51, which is generated by an X-ray tube or the like and is formed into a thin and elongated beam by using a slit, is made monochromatic by means of a monochromater comprising spectroscopic analyzing crystal 52. Here, the glancing angle of incident X-ray beam 51 is made small so that it may come incident to the surface at an angle close to the surface of analyzing crystal 52 and, further, the orientation of analyzing crystal 52 is appropriately selected. As a result, monochromatic X-ray beam 53 emitted from analyzing crystal 52 becomes a widely spaced parallel light beam with an emitting angle which is nearly perpendicular to the crystal surface, and thereby comes incident to a wide area of the surface of silicon (100) wafer 54, the sample to be evaluated. The X-ray beam which enters silicon (100) wafer 54 is diffracted in accordance with Bragg's effect within wafer 54 and emitted from wafer 54. Diffracted X-ray beam 55 then strikes photographic film 56. If no crystal defects exist on or within wafer 54, the diffracted image formed on photographic film 56 is uniform, and, if otherwise, some turbulence will be apparent in this diffracted image. Therefore, the crystal defects existing on and within sample wafer 54 can be detected and evaluated by exposing film 56 to diffracted X-ray beam 55, developing exposed film 56, and finally, examining the diffraction image on the developed film by means of a microscope or the like. According to this method, the incident depth of the monochromatic X-ray beam which comes incident to the sample is on the order of several micrometers, and this range allows extensive information to be obtained regarding the sample as viewed in the direction of its depth.

In recent years, numerous semiconductor devices having a shallow junction have been in practical use. It is important to obtain information regarding crystal defects in the close neighborhood of the surface (within several nanometers in depth) of the semiconductor wafers making up these devices. However, according to the above-described conventional X-ray diffraction micrography, the incident depth of the X-ray beam into the specimen is too great to obtain the information regarding the close neighborhood of the surface.

SUMMARY OF THE INVENTION

Accordingly, an object of the present invention is to provide a method of detecting crystal defects existing in the close neighborhood of the surface of the crystal specimen through the use of X-ray analyzing micrography.

Another object of the present invention is to provide an apparatus which allows the detection of crystal defects existing in the close neighborhood of the surface of the crystal specimen with high sensitivity.

The first object of the present invention may be achieved by a total reflection X-ray micrographic method of detecting and evaluating defects present within a crystal specimen which comprises the steps of utilizing synchrotron radiation, making said synchrotron radiation monochromatic in order to generate a monochromatic X-ray beam, directing said monochromatic X-ray beam into said crystal specimen at a glancing angle smaller than the critical angle of said crystal specimen relative to said monochromatic X-ray beam, and detecting diffracted X-rays from said crystal specimen due to asymmetrical reflection in order to observe the resulting diffracted image.

The secondary object of the invention may be achieved by a total reflection X-ray micrographic apparatus for detecting and evaluating defects present within a crystal specimen which comprises a monochromater into which synchrotron radiation is entered to make said radiation monochromatic in order to generate a monochromatic X-ray beam, a goniometer into which said monochromatic X-ray beam is directed, said goniometer having a rotatable center stage and a rotatable $2\theta$-side stage and retaining said crystal specimen on said center stage, said $2\theta$-side stage being coaxial to said center stage and turning by an angle of $2\theta$ in the same time said center stage turns by an angle of $\theta$, and a diffracted image detection means attached to said $2\theta$-side stage of said goniometer. With this arrangement, a diffracted image of said crystal specimen may be acquired when said monochromatic X-ray beam is directed into said crystal specimen at a glancing angle smaller than the critical angle of said crystal specimen relative to said monochromatic X-ray beam.

The above and other objects, features and advantages of the present invention will become apparent from the following description referring to the accompanying drawings which illustrate an example of a preferred embodiment of the present invention.

DETAILED DESCRIPTION OF A PREFERRED EMBODIMENT

Next, a preferred embodiment of the present invention will be described with specific reference to FIGS. 2 to 4.

Figure 1:
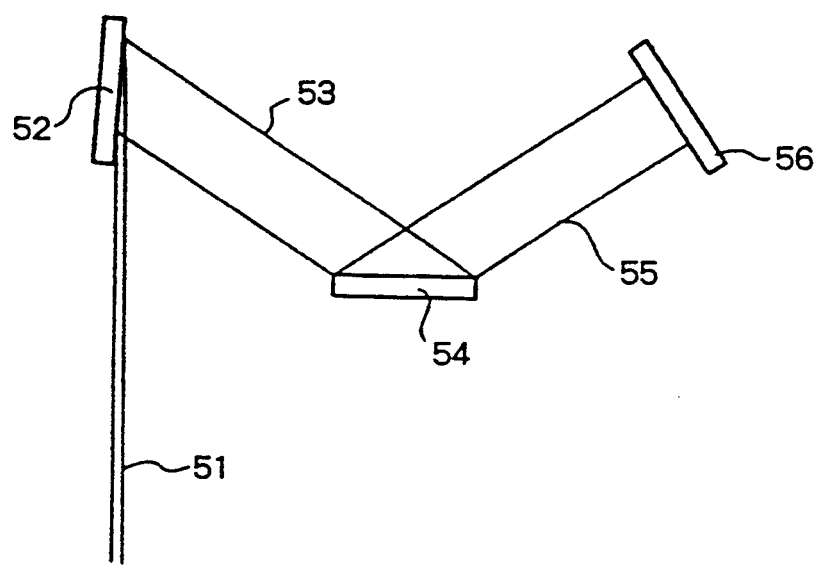
FIG. 1 is a layout plan view showing the manner in which measurement is carried out according to conventional X-ray diffraction micrography.
Figure 2:
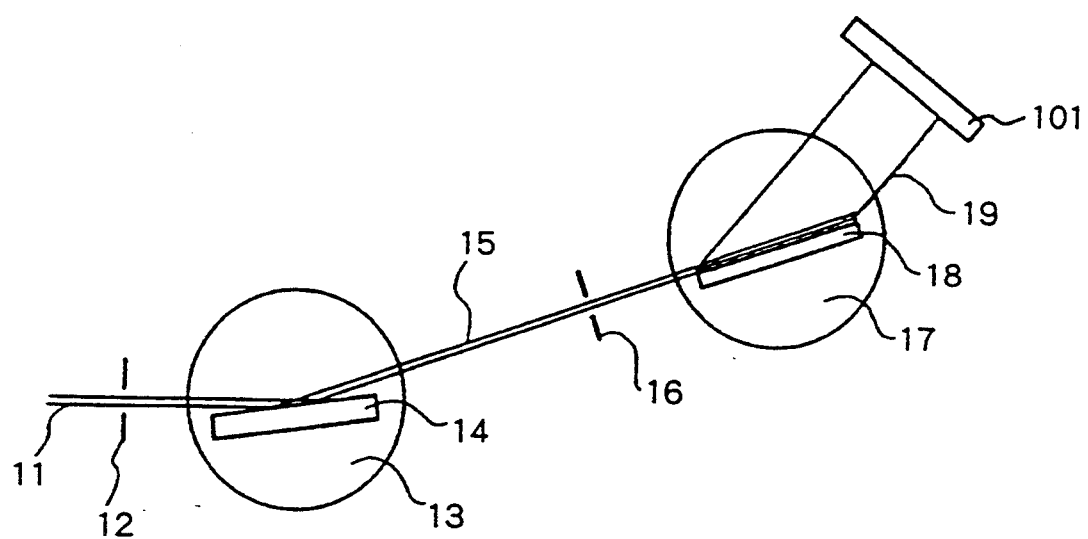
FIG. 2 is a layout plan view illustrating the arrangement of the total reflection X-ray diffraction micrographic apparatus according to a specific embodiment of the present invention.
Figure 3:
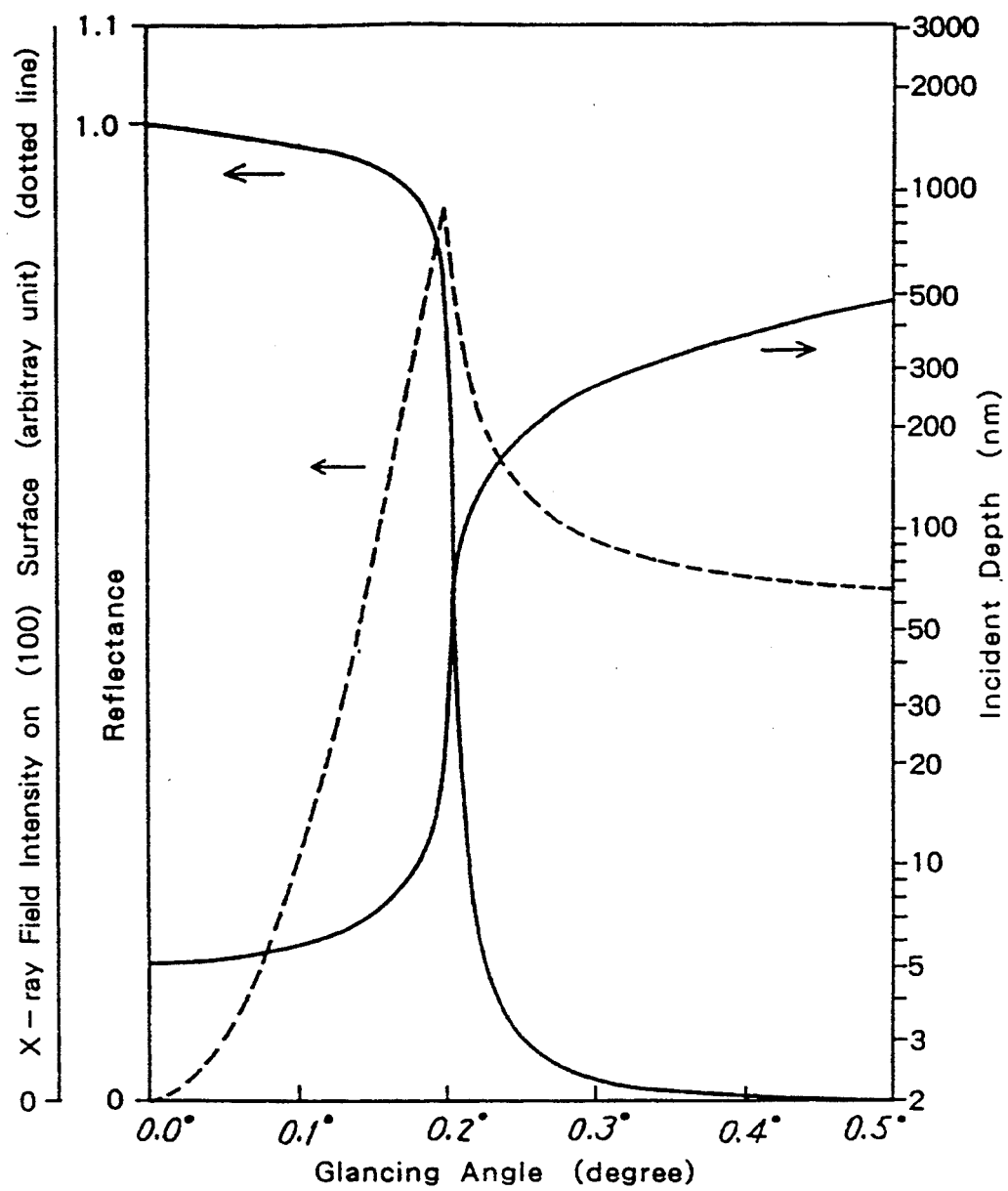
FIG. 3 is a view illustrating the variation of the reflectance on the silicon (100) surface, the incident depth, and the X-ray field intensity on the (100) surface when the glancing angle of the monochromatic X-ray beam relative to the silicon (100) surface is changed with the X-ray beam asymmetrically reflected against the silicon (311) plane.

Referring to the apparatus illustrated in FIG. 2, synchrotron radiation 11 emitted from a synchrotron or a storage ring is formed into beams of rectilinear cross-section by passing the radiation through first slit 12 such that the radiation enters spectroscopic analyzing crystal 14. Crystal 14 is held on the head, that is, the center stage of first goniometer 13 so that it may be turned about the axis of first goniometer 13. Here, first goniometer 13 has two rotatable components which are coaxial and may be turned at angles of $\theta$ and $2\theta$, respectively. Single crystalline of silicon or lithium fluoride, which are commonly used for dispersing the wavelength of light in the X-ray region, may be used as analyzing crystal 14.

At the X-ray emitting side of first goniometer 13, second slit 16 is provided. As can be readily seen by one skilled in the art, when analyzing crystal 14 turns about the axis of first goniometer 13 by an angle of $\theta$, second slit 16 will turn about this axis by an angle of $2\theta$ relative to this axis. As a result, second slit 16 functions to emit a monochromatic X-ray beam 15 of a predetermined size. That is, the monochromater comprises first goniometer 13, analyzing crystal 14 and second slit 16. Naturally, if analyzing crystal 14 is turned by operating first goniometer 13, the wavelength of the monochromatic X-ray beam 15 emitted from this monochromater can be continuously changed.

Second goniometer 17 is provided at the opposite side of first goniometer 13, with second slit 16 interleaved in between. Second goniometer 17 has two rotatable components which can turn by angles of $\theta$ and $2\theta$, respectively, around the center axis. Silicon (100) wafer 18, the specimen to be evaluated, is placed on the center stage of second goniometer 17. Second goniometer 17 should be disposed such that monochromatic X-ray beam 15 which has passed through second slit 16 will precisely enter silicon (100) wafer 18 disposed on its center stage. Therefore, as analyzing crystal 14 of first goniometer 13 turns by an angle of $\theta$, the entire second goniometer 17 will turn about the axis of first goniometer 13 by an angle of $2\theta$. As will be obvious to one skilled in the art, according to this arrangement, second goniometer 17 will effect a planetary motion about first goniometer 13.

Photographic film 101 is provided at the X-ray emitting side of second goniometer 17. When silicon (100) wafer 18 turns about the axis of second goniometer 17 by an angle of $\theta$, this photographic film 101 will turn about this axis by an angle of $2\theta$. As a result, X-ray beam 19 diffracted from silicon (100) wafer 18 will strike photographic film 101. Since the present embodiment utilizes asymmetrical reflection, the position of photographic film 101 relative to silicon (100) wafer 18 should be determined so as to correspond with the orientation of the crystal plane within wafer 18 which will cause asymmetrical reflection.

A total reflection X-ray diffraction micrographic method according to the present invention which uses this apparatus will now be described. We will first consider the theoretical basis of the present invention. Theoretical studies relating to the intensity of asymmetrical reflection occurring when an X-ray beam is entered at a small glancing angle include the following papers:

"Theoretical Considerations on Bragg-case Diffraction of X-rays at a Small Glancing Angle" (Seigo Kishino and Kazutake Kohra, Jpn. J. Apl. Phys., 10(5), 551–557 (1971))

"On X-Ray Diffraction in an Extremely Asymmetric Case" (T. Bedynska, Phys. stat. sol. (a), 19, 365 (1973))

"On the Deviation from Bragg Law and the Widths of Diffraction Patterns in Perfect Crystals" (F. Rustichelli, Phil. Mag., 31, 1 (1975)) and "A Modified Dynamical Theory (MDT) of X-Ray Diffraction in Extremely Asymmetric Schemes" (A. M. Afanasev and O. G. Melikyan, Phys. stat. sol. (a), 122, 459 (1990))

Based on these studies, the intensity of the asymmetric reflection, the incident depth of the X-ray beam or the reflectance of the X-ray can be evaluated when the monochromatic X-ray beam is directed at the silicon (100) surface at an extremely small glancing angle. FIG. 3 illustrates the variations in the reflectance of the silicon (100) surface (indicated by solid line), the incident depth of the X-ray beam (indicated by solid line), and the field intensity of the X-rays on the silicon (100) surface (indicated by dotted line) when the glancing angle of the monochromatic X-ray beam which enters the silicon (100) surface is varied to detect asymmetrical reflection by the silicon (311) plane. These values are calculated in accordance with the technique described by Kishino and Kohra. In this case, since the asymmetrical reflection is to take place at the (311) plane, the wavelength of the monochromatic X-ray beam which enters the silicon (100) surface is varied so as to satisfy diffraction conditions dependent upon the magnitude of the glancing angle. When asymmetrical reflection occurs at the silicon (311) surface, the critical angle $\theta_c$ is equal to 0.20 degrees and, when the glancing angle is greater than the critical angle $\theta_c$, reflectance is practically zero, a fact that reveals that the incident depth of the X-ray beam is within the range of several hundred nanometers. On the other hand, if the glancing angle of the X-ray beam is made smaller than the critical angle $\theta_c$, nearly all of the X-ray beam is reflected (total reflection), indicating that the incident depth of the X-ray beam is in the range of several nanometers. Here, as the glancing angle decreases, the field intensity of the X-rays on the (100) surface increases and reaches a maximum when the glancing angle coincides with the critical angle $\theta_c$. As the glancing angle becomes smaller than the critical angle $\theta_c$, the field intensity decreases linearly. Here, if the glancing angle is smaller than the critical angle $\theta_c$ by 0.05 degrees, that is, if the glancing angle is about 0.15 degrees, it is possible to limit observation to the extreme neighborhood of the surface with sufficient strength of asymmetrical reflection assured since the incident depth will decrease at a greater rate than the field intensity of the X-rays on the (100) surface as the glancing angle is decreased.

Figure 4:
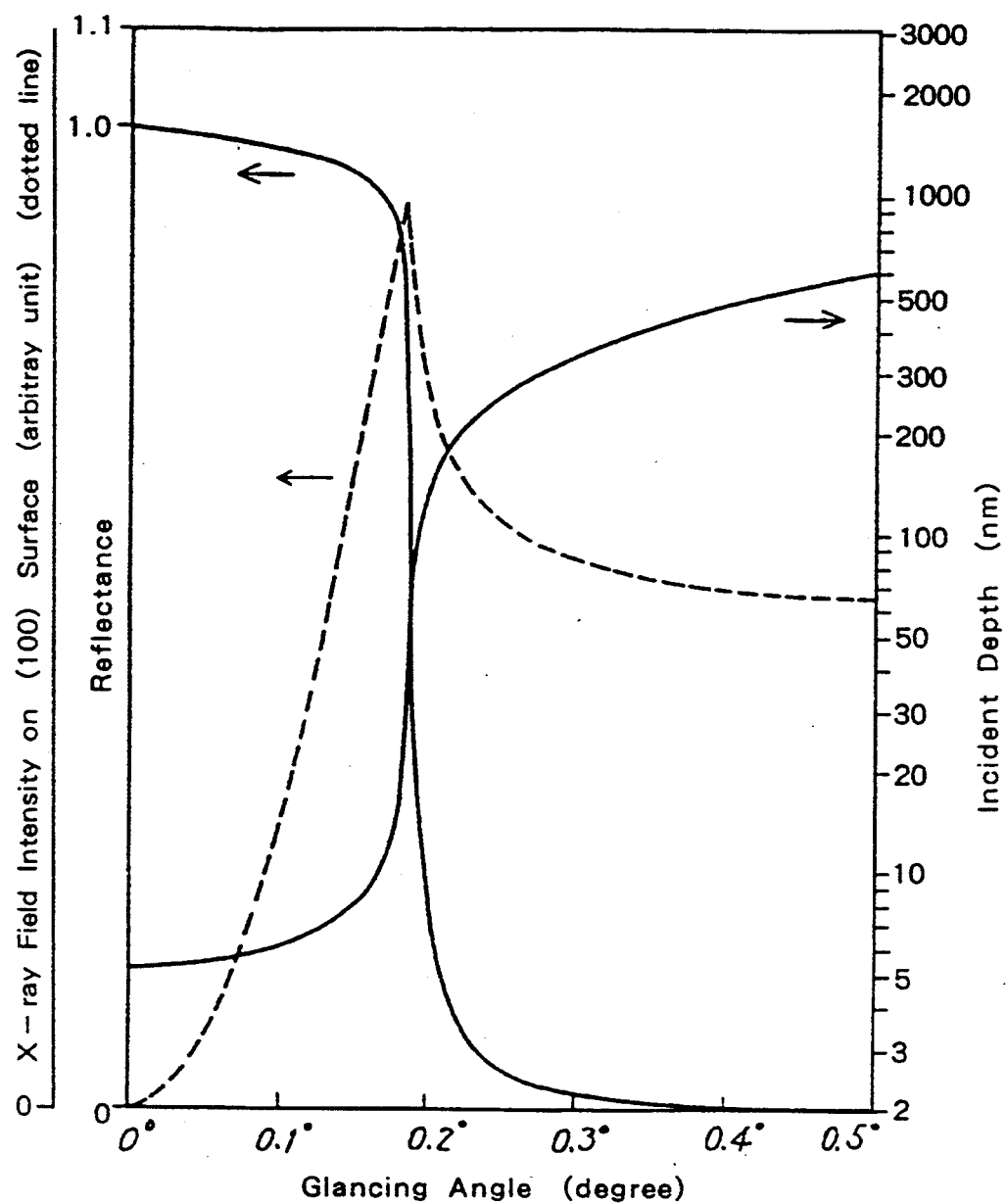
FIG. 4 is a view illustrating the variation of the reflectance on the silicon (100) surface, the incident depth, and the X-ray field intensity on the (100) surface when the glancing angle of the monochromatic X-ray beam relative to the silicon (100) surface is changed with the X-ray beam asymmetrically reflected against the silicon (422) plane.

Likewise, FIG. 4 illustrates the variations of the reflectance (indicated by solid line) on the silicon (100) surface, the incident depth of the X-ray beam (indicated by solid line), and the field intensity of the X-rays on the silicon (100) surface (indicated by dotted line), each evaluated by calculation, when the glancing angle of the monochromatic X-ray beam incident to the silicon (100) surface is varied to detect asymmetrical reflection taking place at the silicon (422) plane. From this figure it can also be seen that, if the glancing angle is smaller than the critical angle $\theta_c$ (=0.18 degrees) by about 0.05 degrees, observation can be effectively limited to only the extreme neighborhood of the surface with sufficient intensity of the asymmetrical reflection maintained.

As will be obvious from the above description, the purpose of the present invention is to detect and evaluate crystal defects present in the extreme neighborhood of the surface based on the diffracted image caused by asymmetrical reflection when the monochromatic X-ray beam is directed into the surface at an angle smaller than the critical angle $\theta_c$, which causes the incident depth of the X-ray beam to be extremely shallow and results in asymmetrical reflection of sufficient intensity. In this case, depending on the kind and orientation of the specimen crystal, the optimum wavelength of the monochromatic X-ray beam differs. In addition, since the glancing angle of the X-ray beam is extremely small, even if a narrow X-ray beam is used, a wide range of the surface of the specimen will be illuminated by the X-ray beam, with the result that the X-ray intensity per unit of the surface area of the specimen will also become small. Therefore, it is necessary to use an X-ray source of great intensity.

FIG. 2 illustrates asymmetrical reflection in which diffraction from a silicon (311) plane inclined by 25.24 degrees relative to the silicon (100) surface is utilized. By operating first goniometer 13, synchrotron radiation 11 can be limited to X-rays having a wavelength of 0.142 nm, and the selected X-rays can be directed into silicon (100) wafer 18 as monochromatic X-ray beam 15. The diffraction angle $\theta_b$ of the silicon (311) plane relative to this monochromatic X-ray beam 15 will be 25.70 degrees, as a result of Bragg's effect reflection. The angle $\alpha$ formed by the silicon (100) surface and the silicon (311) plane will be equal to 25.24 degrees, as described above. In consequence, since the surface of silicon (100) wafer 18 may be regarded as being exactly the silicon (100) crystal plane, second goniometer 17 can be operated so as to direct monochromatic X-ray beam 15 into the silicon (100) wafer 18 at a glancing angle of 0.46 degrees (=$\theta_b - \alpha$). Thus, diffracted X-rays 19 from the silicon (311) plane can be observed at the position corresponding to the above-described Bragg's reflection angle. As can be seen from FIG. 3, the incident depth of monochromatic X-ray beam 15 into silicon (100) wafer 18 will then be approximately several hundred nanometers. Here, if wavelength of the monochromatic X-ray beam 15 is slightly shortened by sequentially turning first goniometer 13 to the small-angle side, the diffraction angle $\theta_b$ from the silicon (311) plane caused by asymmetrical reflection in second goniometer 17 will also decrease correspondingly. As a result, it is possible to decrease the glancing angle of monochromatic X-ray beam 15 relative to the surface of silicon (100) wafer 18 and, ultimately, decrease it to an angle smaller than the critical angle $\theta_c$ at which total reflection takes place without losing sight of diffracted X-rays 19. This operation is achieved by carefully utilizing the continuity of the wavelength of the synchrotron radiation, as will be described later.

If this operation is carried out until the wavelength $\lambda$ of monochromatic X-ray beam 15 becomes approximately 0.1404 nm, the glancing angle of monochrome X-ray beam 15 relative to silicon (100) wafer 18 will reach 0.15 degrees, which is smaller than the critical angle $\theta_c$ (=0.20 degrees) in this case. As is obvious from FIG. 3, the reflectance of monochromatic X-ray beam 15 will then approach 1 while the field strength of the X-rays on the surface of silicon (100) wafer 18 will also be sufficiently great. The incident depth of monochromatic X-ray beam 15 will be several nanometers, and only information regarding the extreme neighborhood of the surface will be contained within the diffracted X-rays 19. In this way, crystal defects present in the extreme neighborhood of the surface of silicon (100) wafer 18 can be detected and evaluated by exposing photographic film 101 to diffracted X-rays 19, developing the film, and observing the photographed diffracted image by means of a microscope or the like.

As described above, the glancing angle of the monochromatic X-ray beam is initially made greater than the critical angle $\theta_c$ and is gradually decreased to an angle smaller than the critical angle $\theta_c$ for measurement, because if the measurement is initially conducted at an angle smaller than the critical angle $\theta_c$, it will be extremely difficult to find the diffracted X-ray due to the asymmetrical reflection of interest. This is due to the fact that, if the glancing angle is smaller than the critical angle $\theta_c$, the intensity of the diffracted X-rays due to asymmetric reflection will be smaller than for high angles, and diffracted X-rays from other crystal planes or X-rays of high-order diffraction may easily be included.

The reason for using synchrotron radiation will now be described. In the case of this embodiment, since the wavelength of the monochromatic X-ray beam is changed in order to capture the asymmetrically diffracted X-rays of interest, it is not possible to simply use any characteristic X-ray beam of fixed wavelength. In addition, since the glancing angle is extremely small, an X-ray beam of great intensity is needed. The only available method for continuously changing the wavelength of light in the X-ray region is changing the wavelength selected by the monochromater by using a X-ray source of continuous spectrum. Therefore, in this embodiment, it is necessary to use an extremely intense X-ray source of continuous spectrum. As such an X-ray source, obviously, synchrotron radiation is the only option.

We will now turn our attention to another asymmetrical reflection in which diffraction from the silicon (422) plane inclined by an angle of 35.26 degrees relative to the silicon (100) surface is utilized. Again, the observed effect is similar to the case in which asymmetrical reflection from the silicon (311) plane is utilized.

The procedure utilized is similar to the procedure followed for asymmetrical reflection from the silicon (311) plane described above in which, eventually, X-rays of a wavelength in the neighborhood of 0.1284 nm are selected from the synchrotron radiation to obtain monochromatic X-ray beam 15. The glancing angle of this monochromatic X-ray beam 15 relative to silicon (100) wafer 18 reaches 0.13 degrees, an angle smaller than the critical angle $\theta_c$ (=0.18 degrees) for this case. As can be seen from FIG. 4, the reflectance of monochromatic X-ray beam 15 will then approach 1, and the field intensity of the X-rays on the surface of wafer 18 will be sufficiently great. The incident depth of X-ray beam 15 will be several nanometers, and only information regarding the extreme neighborhood of the surface will be contained within diffracted X-rays 19. Crystal defects present in the extreme neighborhood of the surface of the silicon (100) wafer 18 can be detected and evaluated by developing photographic film 101 that has been exposed to diffracted X-rays 19 and examining the photographed diffracted image by means of a microscope or the like.

Although the specific embodiment of the present invention herein described involves a case using a silicon (100) wafer as the specimen, the present invention can also be applied to silicon wafers having other surface crystal orientations, to semiconductor wafers other than wafers made of silicon, or to any other crystalline materials. Similarly, the crystal plane which causes the asymmetrical reflection is not restricted to the (311) plane or (422) plane. Based on the above description, the proper arrangement for implementing the method according to the present invention to specimens other than silicon (100) wafers will be readily apparent to one skilled in the art. Further, as the means for making the synchrotron radiation monochromatic, monochromaters using two parallel spectroscopic crystals other than the above-described goniometer and single spectroscopic analyzing crystal may be used.

It is to be understood that variations and modifications of the total reflection X-ray diffraction micrographic method and apparatus disclosed herein will be evident, to those skilled in the art. It is intended that all such modifications and variations be included within the scope of the appended claims.

What is claimed is:

1. A total reflection X-ray diffraction micrographic method of detecting and evaluating defects present within a crystal specimen comprising the steps of:

utilizing continuous wavelength spectrum synchrotron radiation;

making said synchrotron radiation monochromatic in order to generate monochromatic X-ray beam;

directing said monochromatic X-ray beam first into said crystal specimen at a glancing angle greater than the critical angle of said crystal specimen relative to said monochromatic X-ray beam, and then directing said monochromatic X-ray beam into said crystal specimen at a glancing angle smaller than said critical angle by turning said crystal specimen and by successively changing the wavelength of the monochromatic X-ray while continuously satisfying Bragg's condition; and detecting diffracted X-rays from said crystal specimen due to asymmetrical reflection in order to observe the resulting diffracted image.

2. A total reflection X-ray diffraction micrographic method as set forth in claim 1 wherein said crystal specimen is retained by a goniometer which has two rotatable components, one of said components being able to turn by an angle of $\theta$ in the same time that the other turns by an angle of $2\theta$.

3. A total reflection X-ray diffraction micrographic method as set forth in claim 2 wherein said monochromatic X-ray beam is produced by making said synchrotron radiation monochromatic by means of a goniometer provided with a spectroscopic analyzing crystal.

4. A total reflection X-ray diffraction micrographic method as set forth in claim 2 wherein said crystal specimen is a semiconductor wafer used for making a semiconductor device.

5. A total reflection X-ray diffraction micrographic method as set forth in claim 4 wherein said semiconductor wafer is a silicon (100) wafer.

6. A total reflection X-ray diffraction micrographic method as set forth in claim 5 wherein said diffracted X-rays are produced by asymmetric reflection of said monochromatic X-ray beam by a silicon (311) plane.

7. A total reflection X-ray diffracted micrographic method as set forth in claim 5 wherein said diffracted X-rays are produced by asymmetric reflection of said monochromatic X-ray beam by a silicon (422) plane.

* * * * *